United States Patent [19]
Hill

[11] Patent Number: 5,678,832
[45] Date of Patent: Oct. 21, 1997

[54] BORON NITRIDE SEAL AND METHOD OF USE

[75] Inventor: Richard Frank Hill, Chagrin Falls, Ohio

[73] Assignee: Advanced Ceramics Corporation, Lakewood, Ohio

[21] Appl. No.: 580,860

[22] Filed: Dec. 29, 1995

[51] Int. Cl.[6] ............................ F16J 15/02; C04B 35/64
[52] U.S. Cl. ............................ 277/227; 277/DIG. 6; 501/96
[58] Field of Search ........................ 277/DIG. 6, 227; 501/96

[56] References Cited

U.S. PATENT DOCUMENTS

| | | | |
|---|---|---|---|
| 4,634,640 | 1/1987 | Hunold et al. | 428/704 |
| 5,010,045 | 4/1991 | Maya | 501/96 |
| 5,116,589 | 5/1992 | Hoenig | 423/298 |
| 5,328,875 | 7/1994 | Ueda et al. | 501/87 |
| 5,462,291 | 10/1995 | Maeda et al. | 277/100 |

*Primary Examiner*—William A. Cuchlinski, Jr.
*Assistant Examiner*—Christina Annick
*Attorney, Agent, or Firm*—Eugene Lieberstein; Michael N. Meller

[57] ABSTRACT

Boron nitride formed to an optimum density and composition of soluble borates and oxygen forms a material which deforms under pressure and reforms to make a very low permeability seal. The boron nitride seal is formed by precompacting a boron nitride powder having a soluble borate concentration of between 0.5 and 1.90% by weight, hot pressing the powder to a density of about 1.85 g/cc and machining the hot pressed powder into a seal of desired shape.

5 Claims, 1 Drawing Sheet

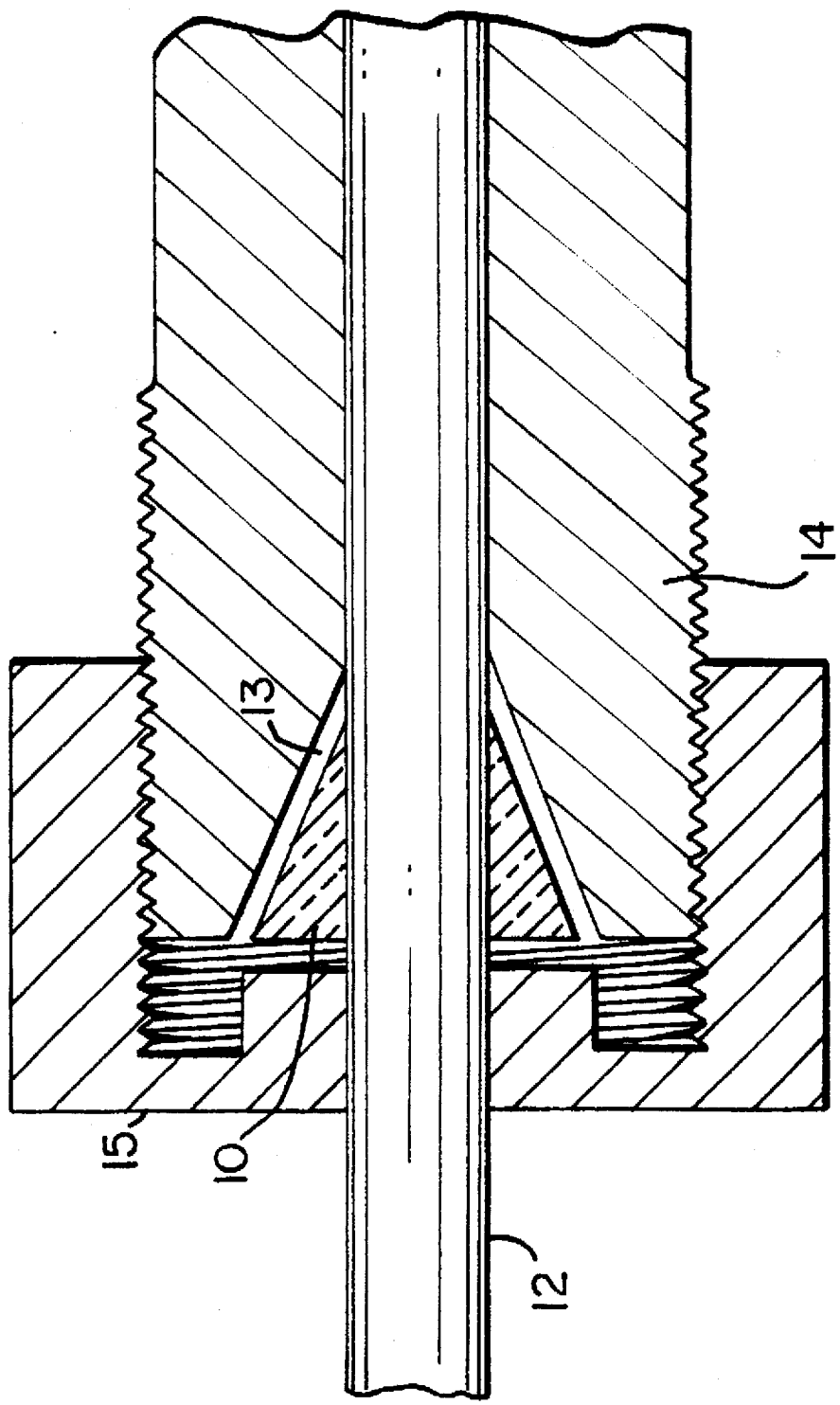

BORON NITRIDE SEAL AND METHOD OF USE

FIELD OF INVENTION

This invention relates to boron nitride for use as a seal and to a method of forming a deformable seal of boron nitride.

BACKGROUND OF THE INVENTION

Boron nitride or boron nitride composites are not commercially used to form pressure seals due to their inability to deform and reform under pressure. It has been discovered in accordance with the present invention that boron nitride or boron nitride composites containing soluble borates when hot pressed to within a specified narrow density range may be machined into a suitable shape which can be deformed under pressure and reformed to make a low permeability seal. A boron nitride seal is resistant to hostile exhaust gases and does not react with fuel such as gasoline, is electrically insulating and will withstand high temperature.

One specific application for a boron nitride seal is to seal oxygen sensors in internal combustion engines. Oxygen sensors control the air to fuel ratio in internal combustion engines and minimize environmental pollutants. The most common oxygen sensor mechanism utilizes a zirconia ceramic to determine whether the oxygen in the exhaust gas stream is oxygen rich or deficient. The sensor compares the exhaust gas oxygen to clean reference air. The reference air must be separated from the exhaust gases by a seal around the zirconia ceramic. At present oxygen sensors are sealed with soft ceramics such as steatite or talc that can be formed into a suitable shape and then pressed into the sensor housing between the zirconia ceramic and the housing. This seal is not ideal and tends to leak in that it can be permeated by the components of the exhaust gases.

SUMMARY OF THE INVENTION

A low permeability boron nitride ceramic composition has been discovered for use as a material which deforms under pressure and reforms to make a comprising boron nitride having a density in the range of 1.5–1.9 g/cc, soluble borates in an amount of 0.5–1.9% by weight and a total oxygen concentration of 1.0–2.5% by wt.

A method has also been discovered for forming a deformable boron nitride ceramic seal comprising the steps of: precompacting a boron nitride powder having a soluble borate concentration of between 0.5 and 1.90% by weight, hot pressing the powder to a density of about 1.85 g/cc and machining the hot pressed powder into a seal of desired shape.

BRIEF DESCRIPTION OF THE DRAWINGS

Other advantages of the present invention will become apparent from the following detailed description of the invention when read in conjunction with the accompanying drawing illustrating the use of a boron nitride seal in a tubing system requiring an inert seal.

DETAILED DESCRIPTION OF THE INVENTION

It has been discovered in accordance with the present invention that boron nitride or boron nitride composites can be hot pressed into a suitable shape or thereafter machined into a desired shape for use as a seal particularly for use under conditions of high pressure and/or high temperatures. Boron nitride will form a less permeable and less reactive seal to high temperature such as from the hot exhaust gas of an internal combustion engine than seals of currently used ceramic materials such as zirconia ceramics or talc. It has been further discovered that when the hot pressed boron nitride is of a composition containing soluble borate in a specified range and of a specified density and oxygen concentration it is capable of being compacted under pressure so as to deform and reform itself into an impermeable seal.

An application for a boron nitride seal in accordance with the present invention is shown in the accompanying drawing in which boron nitride is shaped into a ferrule 10 for use in sealing tubing 12. The tubing 12 may be of any metal composition such as copper or of a ceramic composition. The boron nitride ferrule 10 is mounted over the tubing 12 and loosely fitted into a substantially conical gap or opening 13 of a tubular pipe fitting 14. The pipe fitting 14 has external threads for engaging the internal threads of a nut 15. Upon tightening the nut 15 the conical end of the fitting 14 and ferrule 10 are squeezed in place against the tubing 12 causing the ferrule 10 to deform in situ and to reform filling up the gap 13 to form an impermeable seal.

The boron nitride seal is formed from conventional commercially available boron nitride powder which is known to contain boric oxide. To produce a boron nitride sealing material the boron nitride powder must be hot pressed at a desired temperature under specified pressure conditions to produce a material having the following properties:

Density 1.5–1.9 g/cc

Soluble Borates 0.5–1.9% by wt.

Oxygen 1.0–2.5% by wt.

The composite may be hot pressed into any desired geometry for use as a seal or may be machined into any desired shape after being hot pressed. The temperature and pressure conditions must be selected to cause the density to fall within the above range. The soluble borate concentration corresponds to the concentration of oxygen and boric oxide in the boron nitride raw material powder before hot pressing. The concentration of soluble borates in the hot pressed boron nitride has been found to be critical in forming a satisfactory sealing material which can under high pressure deform and reform itself. The boric oxide and density concentrations control the malleability of the material so that it is neither too hard or too soft for use as a seal. The preferred concentration of soluble borate in the hot pressed boron nitride composite is 0.9+/–0.3% by weight with a preferred total oxygen concentration of 1.6+/–0.25% by weight and a preferred density of 1.85+/–0.1 g/cc.

The preferred process for making the boron nitride seal of the present invention with the preferred concentration of soluble borate in weight percent is to use a blend of commercial BN powders having different oxygen concentrations. A suitable blend was formulated as follows:

50% BN powder with oxygen of 0.5+/–0.2%

50% BN powder with oxygen of 2.7+/–0.3%

The blend of BN powder was precompacted and hot pressed at 1800° C. under pressure of 2000 psi in a graphite mold. The temperature may range generally from 1500° C. to 2100° C. although an operating temperature between 1700° C. to 1850° C. is preferred at a pressure of between 1000 psi to 3000 psi. The oxygen concentration level in the precompacted boron nitride powder relates to the final oxygen level in the hot pressed shape. For purposes of comparison the typical properties of conventional hot pressed boron nitride ("HBN"), a hot pressed composite of mullite and boron nitride ("MBN"), a hot pressed calcium glass boron nitride ("HBR") and a variation test grade of the conventional hot pressed boron nitride ("HBT") was compared to that of the hot pressed boron nitride of the present invention ("PHBT") as shown below:

| Typical Properties | HBR | HBN | PHBT | HBT |
|---|---|---|---|---|
| Density g/cc | 1.95 | 2.05 | 1.85 | 1.85 |
| Soluble Borates % | 1.90 | 2.20 | 0.90 | 0.2 |
| Total Oxygen % | 2.50 | 2.80 | 1.60 | 0.6 |

The properties of MBN are not listed because mullite is an oxide material of aluminum and silica so that the resulting properties on density, oxygen and soluble borate are not comparable. MBN proved to be much too hard for use as a seal. HBR as well as MBN are hard and brittle and under pressure had a tendency to crack. The HBR, HBT and MBN materials failed to form an effective seal. Only PHBT forms an effective seal.

What we claim is:

1. A low permeability boron nitride ceramic composition for use in forming a deformable seal from said boron nitride composition under the application of pressure with the composition of said deformable seal prior to the application of pressure consisting essentially of boron nitride having a density in the range of 1.5–1.90 g/cc, soluble borates in an amount of 0.5–1.9% by weight and a total oxygen concentration of 1.0–2.0% by wt.

2. A low permeability boron nitride ceramic composition as defined in claim 1 consisting essentially of boron nitride having a density of 1.85+/−0.1 g/cc, soluble borates in an amount of 0.9+/−0.1% by weight and a total oxygen concentration of 1.6+/−0.25% by wt.

3. A boron nitride composition for forming a deformable ceramic seal as defined in claim 1 comprising a blended composite of boron nitride particles having a total oxygen concentration of 0.5+/−0.2% by weight and boron nitride particles having a total oxygen concentration of 2.7%+/−0.3% by weight with the blended composite having a density in the range of 1.5–1.9 g/cc and a soluble borate concentration of between 0.5 and 1.90%.

4. A method of forming a deformable ceramic boron nitride seal consisting essentially of the steps of: precompacting a boron nitride powder having a soluble borate concentration of between 0.5 and 1.90% by weight, hot pressing the powder to a density of about 1.85 g/cc and machining the hot pressed powder into a seal of desired shape.

5. A boron nitrite ferrule surrounding a fitting around a length of tubing composed solely of a shaped boron nitride composition consisting essentially of boron nitride having a density of 1.85+/−0.1 g/cc, soluble borates in an amount of 0.9+/−0.1% by weight and a total oxygen concentration of 1.6+/−0.25% by wt.

* * * * *